(12) United States Patent
Jang et al.

(10) Patent No.: US 8,837,801 B2
(45) Date of Patent: *Sep. 16, 2014

(54) MULTI-ENERGY X-RAY SYSTEM, IMAGE PROCESSING APPARATUS FOR DISCRIMINATING MULTI-ENERGY X-RAY MATERIAL, AND IMAGE PROCESSING METHOD FOR MATERIAL DISCRIMINATION OF MULTI-ENERGY X-RAY SYSTEM

(75) Inventors: Kwang Eun Jang, Yongin-si (KR); Young Hun Sung, Yongin-si (KR); Jong Ha Lee, Yongin-si (KR); Sung Su Kim, Yongin-si (KR); Seok Min Han, Yongin-si (KR); Dong-Goo Kang, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 109 days.

This patent is subject to a terminal disclaimer.

(21) Appl. No.: 13/395,514

(22) PCT Filed: Sep. 13, 2010

(86) PCT No.: PCT/KR2010/006197
§ 371 (c)(1),
(2), (4) Date: Mar. 12, 2012

(87) PCT Pub. No.: WO2011/037344
PCT Pub. Date: Mar. 31, 2011

(65) Prior Publication Data
US 2012/0170826 A1    Jul. 5, 2012

(30) Foreign Application Priority Data
Sep. 22, 2009  (KR) .......................... 10-2009-0089355

(51) Int. Cl.
*G06K 9/00* (2006.01)
*A61B 6/00* (2006.01)
*A61B 6/03* (2006.01)

(52) U.S. Cl.
CPC ................. *A61B 6/00* (2013.01); *A61B 6/4241* (2013.01); *A61B 6/482* (2013.01); *A61B 6/4007* (2013.01); *A61B 6/03* (2013.01)
USPC ....................................................... 382/132

(58) Field of Classification Search
None
See application file for complete search history.

(56) References Cited

U.S. PATENT DOCUMENTS

| | | | |
|---|---|---|---|
| 6,507,633 B1* | 1/2003 | Elbakri et al. ..................... 378/8 |
| 6,614,874 B2* | 9/2003 | Avinash .......................... 378/62 |
| 2003/0156684 A1* | 8/2003 | Fessler ........................... 378/210 |
| 2009/0052762 A1* | 2/2009 | Dugan et al. .................. 382/132 |
| 2009/0147919 A1* | 6/2009 | Goto et al. ........................ 378/86 |
| 2010/0232669 A1* | 9/2010 | Ziegler et al. ................. 382/132 |

FOREIGN PATENT DOCUMENTS

| | | |
|---|---|---|
| JP | 2004-160228 A | 6/2004 |
| JP | 2007-044275 A | 2/2007 |
| JP | 2009-125250 A | 6/2009 |

OTHER PUBLICATIONS

Zhenyu Zhou; Richard M. Leahy; and Jinyi Qi, "Approximate Maximum Likelihood Hyperparameter Estimation for Gibbs Priors", Jun. 1997, IEEE Transactions on Image Processing, vol. 6, No. 6, pp. 844-861.*

International Search Report issued Apr. 29, 2011, in counterpart International Application No. PCT/KR2010/006197 (2 pages).

* cited by examiner

*Primary Examiner* — Bhavesh Mehta
*Assistant Examiner* — Siamak Harandi
(74) *Attorney, Agent, or Firm* — NSIP Law (57) ABSTRACT

Disclosed are a multi-energy x-ray system, an image processing apparatus for discriminating a multi-energy x-ray material, and an image processing method for material discrimination of a multi-energy x-ray system. The image processing apparatus for discriminating a multi-energy x-ray material according to one aspect of the present invention comprises: a table for recording attenuation information and multi-energy x-ray spectrum information which correspond to one or more materials; an initial image estimating portion for estimating an initial image of each of the materials with respect to a projection image of each of the energy bands generated when a multi-energy x-ray spectrum passes through a detecting target formed with one or more materials; and an image update portion for updating the initial image as the material discrimination image using the estimated initial image and the spectrum information recorded in the table and the attenuation information recorded in the table.

16 Claims, 6 Drawing Sheets

MULTI-ENERGY X-RAY SYSTEM, IMAGE PROCESSING APPARATUS FOR DISCRIMINATING MULTI-ENERGY X-RAY MATERIAL, AND IMAGE PROCESSING METHOD FOR MATERIAL DISCRIMINATION OF MULTI-ENERGY X-RAY SYSTEM

TECHNICAL FIELD

Example embodiments relate to a multi-energy x-ray system, an apparatus for discriminating a multi-energy x-ray material from an image, and a method of processing a material-discriminated image in the multi-energy x-ray system.

BACKGROUND ART

A large number of x-ray systems may display images using attenuation characteristics that are detected by passing an x-ray having a single energy band through a target. In such x-ray systems, when materials forming the target have different attenuation characteristics, high quality images may be acquired. Conversely, when the materials have similar attenuation characteristics, an image quality may be degraded.

A multi-energy x-ray system may acquire an x-ray image having at least two energy bands. In general, since materials show different x-ray attenuation characteristics in different energy bands, a separation of images for each material may be performed using the x-ray attenuation characteristics.

Currently, a Computed Tomography (CT) scanner or a nondestructive inspector having a dual energy source or a dual energy separation detector has emerged. In these devices, a density image for materials forming a target may be acquired by rotating a source by at least 180° on the target. In such a dual-energy CT device, an image having a regular quality may be acquired using a relatively simple scheme of adding, subtracting, or segmenting acquired images and masking pseudo-colors.

DISCLOSURE OF INVENTION

Technical Solutions

According to example embodiments, there is provided an apparatus for discriminating a multi-energy x-ray material from an image, the apparatus including a table to record attenuation information and multi-energy x-ray spectrum information corresponding to at least one material, an initial image guessing unit to guess an initial image of each of the at least one material with respect to a projection image of each energy band that is generated when a multi-energy x-ray spectrum passes through a target consisting of the at least one material, and an image updating unit to perform an update of the initial image to a material-discriminated image, based on the guessed initial image, the spectrum information recorded in the table, and the attenuation information recorded in the table.

According to example embodiments, there is also provided a method of acquiring a multi-energy x-ray image, the method including receiving a projection image of each energy band that is generated when a multi-energy x-ray spectrum passes through a target consisting of at least one material, guessing an initial image for each of the at least one material based on the projection image, and acquiring a material-discriminated image with respect to each of the at least one material, by applying an image updating algorithm to the initial image.

According to example embodiments, there is also provided a multi-energy x-ray system, including a multi-energy x-ray equipment unit to radiate a multi-energy x-ray spectrum, and a material-discriminated image processing unit to acquire a material-discriminated image with respect to each of at least one material, by receiving a projection image of each energy band that is generated when the multi-energy x-ray spectrum passes through a target consisting of the at least one material. Here, the material-discriminated image processing unit may include a table to record attenuation information and multi-energy x-ray spectrum information corresponding to the at least one material, an initial image guessing unit to guess an initial image of each of the at least one material with respect to the projection image of each energy band that is generated when the multi-energy x-ray spectrum passes through the target consisting of the at least one material, and an image updating unit to update the initial image as the material-discriminated image, based on the guessed initial image, the spectrum information recorded in the table, and the attenuation information recorded in the table.

Effects of Invention

Example embodiments provide a multi-energy x-ray system that may acquire material-discriminated images.

Example embodiments also provide a multi-energy x-ray system that may measure data such as a bone density, an amount of body fat, an amount of water weight, or the like when a target corresponds to a tissue of a human body, and the like.

Example embodiments also provide an apparatus for discriminating a multi-energy x-ray material from an image, which is used in the foregoing multi-energy x-ray system.

Example embodiments also provide a multi-energy x-ray system that may acquire x-ray images of high quality and high contrast in medical imaging devices.

Example embodiments also provide a multi-energy x-ray system that may acquire material-discriminated images that may be applied to a conventional dual energy Computed Tomography (CT).

BEST MODE FOR CARRYING OUT THE INVENTION

Reference will now be made in detail to example embodiments, examples of which are illustrated in the accompanying drawings, wherein like reference numerals refer to the like elements throughout. Example embodiments are described below in order to explain example embodiments by referring to the figures.

A multi-energy x-ray system according to embodiments may denote a system using at least two x-ray sources or using an x-ray detector that enables a separation of images for each of two energy bands or more, or using a combination of the at least two x-ray sources and the x-ray detector. The multi-energy x-ray system may be implemented by one of a radiography system, a tomosynthesis system, a Computed Tomography (CT) system, and a nondestructive inspector. However, these systems are merely examples. It may be well understood by those skilled in the art that the multi-energy x-ray system according to embodiments may be implemented by various types and means.

Figure 1:
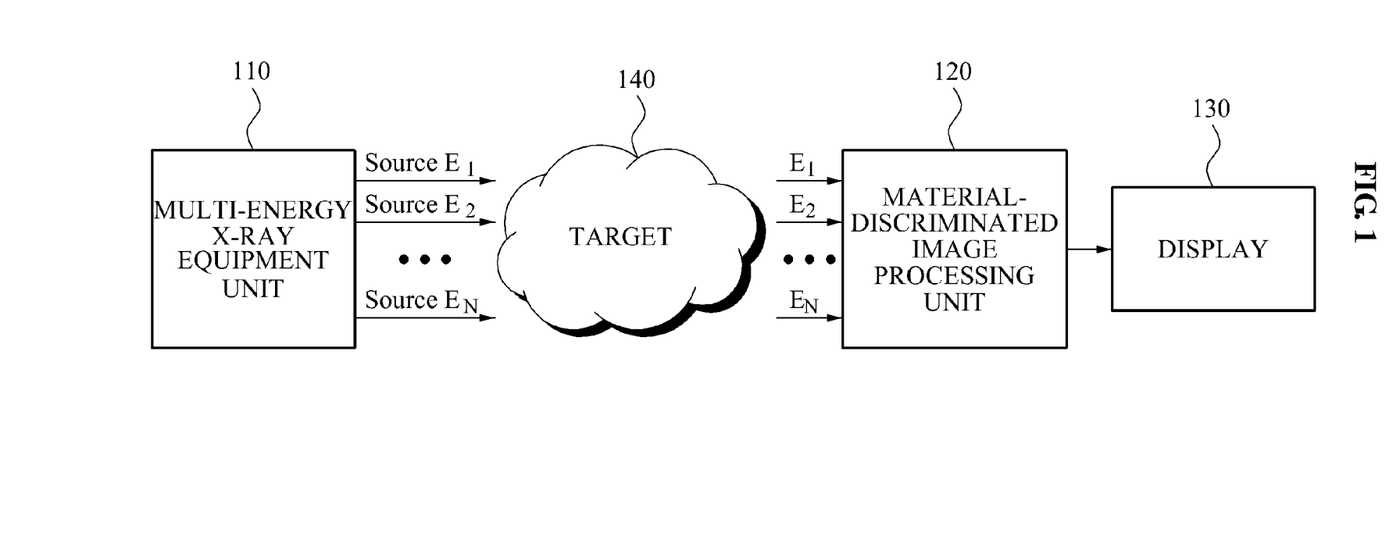
FIG. 1 is a diagram illustrating a multi-energy x-ray system according to embodiments.

FIG. 1 illustrates a multi-energy x-ray system according to embodiments.

Referring to FIG. 1, the multi-energy x-ray system includes a multi-energy x-ray equipment unit 110, and a material-discriminated image processing unit 120. Depending on configuration schemes, the material-discriminated image processing unit 120 may include a display 130 to display an acquired material-discriminated image, or may be connected with the display 130 through an image input terminal and an image output terminal to display the acquired material-discriminated image.

The multi-energy x-ray equipment unit 110 may be configured using schemes as follows:

(1) a source scheme of using a plurality of sources having different spectrum characteristics;

(2) a detector scheme of measuring x-ray quanta incident at a detector end, for each energy band; and (3) a source-detector hybrid scheme of using an x-ray source having N1 energy bands, and using a detector that may discriminate N2 energy bands.

A multi-energy x-ray spectrum may be radiated by the multi-energy x-ray equipment unit 110 that may be configured using one of the three foregoing schemes. Respective projection images of energy bands that may be generated when the multi-energy x-ray spectrum passes through a target consisting of at least one material may be processed as image signals by the material-discriminated image processing unit 120. Also, material-discriminated images may be output through the display 130.

The multi-energy x-ray spectrum may denote various spectrums depending on the schemes of configuring the multi-energy x-ray equipment unit 110, for example, (1) an x-ray spectrum radiated by a source in the source scheme, (2) a spectrum of each energy band received from a detector in the detector scheme, and (3) both an x-ray spectrum radiated by a source and a spectrum of each energy band detected by a detector in the source-detector hybrid scheme.

<Operation of Material-Discriminated Image Processing Unit>

Figure 2:
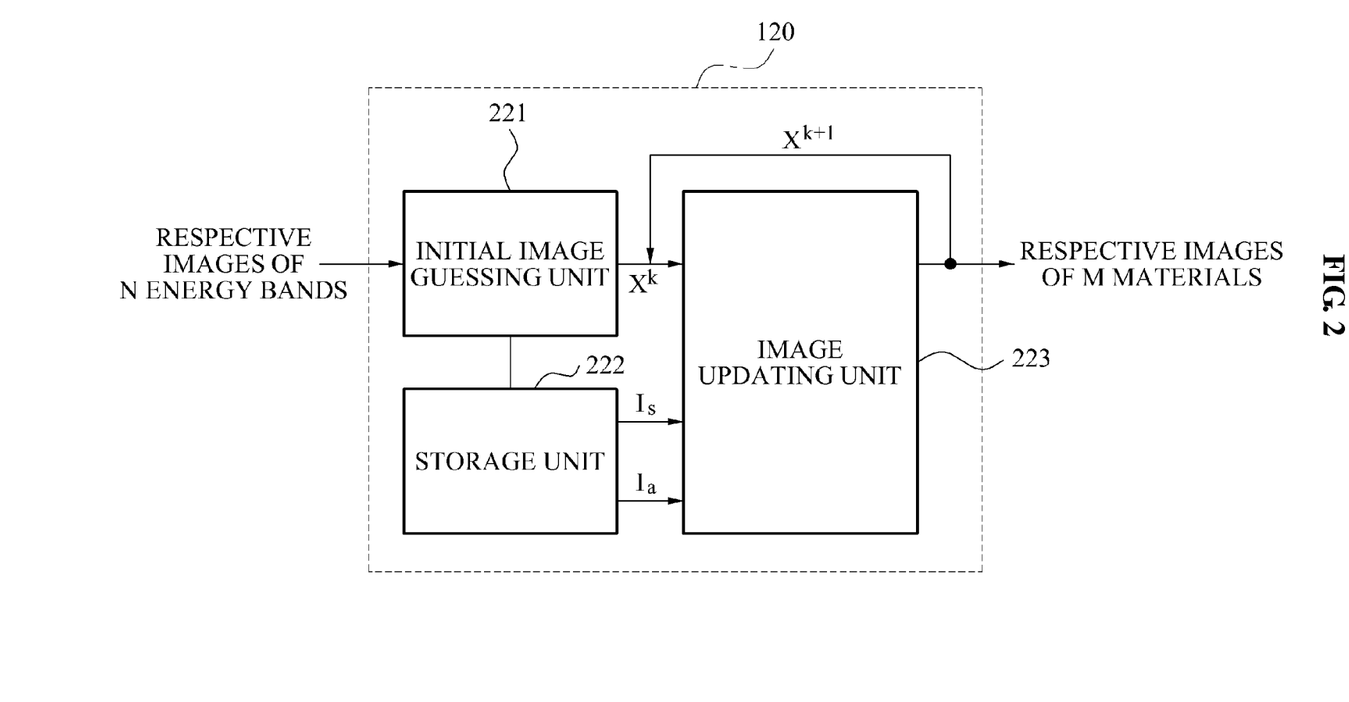
FIG. 2 is a diagram illustrating a material-discriminated image processing unit of a multi-energy x-ray system according to embodiments.

FIG. 2 illustrates a material-discriminated image processing unit according to embodiments.

According to embodiments, the material-discriminated image processing unit 120 illustrated in FIG. 1 includes an initial image guessing unit 221, a storage unit 222, and an image updating unit 223.

The initial image guessing unit 221 may generate an initial image for each of M materials forming a target 140, by receiving an input of projection images of each energy band that may be generated when a multi-energy x-ray spectrum of the multi-energy x-ray equipment 110 of FIG. 1 passes through the target 140 consisting of the at least one material. The initial image guessing unit 221 may guess the initial image using energy distribution information for each of the at least one material forming the target 140.

The storage unit 222 may record attenuation information and spectrum information of the multi-energy x-ray equipment unit 110 corresponding to at least one material. The attenuation information $I_A$ and the spectrum information $I_S$ that are recorded in the storage unit 222 may be input to the image updating unit 223 to be used for updating the initial image output from the initial image guessing unit 221. According to embodiments, the spectrum information stored in the storage unit 222 may be recorded in an external storage unit, depending on configuration. However, the storage unit 222 described herein may refer to a logical location, as opposed to a physical location in which pieces of corresponding information may be recorded in actuality.

The image updating unit 223 may perform an update of the initial image to a material-discriminated image, based on the initial image guessed by the initial image guessing unit 221, the spectrum information recorded in the storage unit 222, for example, a table, and the attenuation information recorded in the storage unit 222. In an image updating procedure performed by the image updating unit 223, a method of calculating a correction value by which a predetermined cost function may be minimized, and updating the initial image to the material-discriminated image by applying the calculated correction value to the initial image may be employed. In one aspect, the image updating unit 223 may perform the update based on pixels constituting an image, that is, a pixel by pixel based update. However, depending on configurations, the update may be performed based on blocks, or images. That is, a block by block based update or an image by image based update may be performed. Herein, by way of example, operation of the image updating unit 223 will be described based on the pixel by pixel based case.

Figure 3:
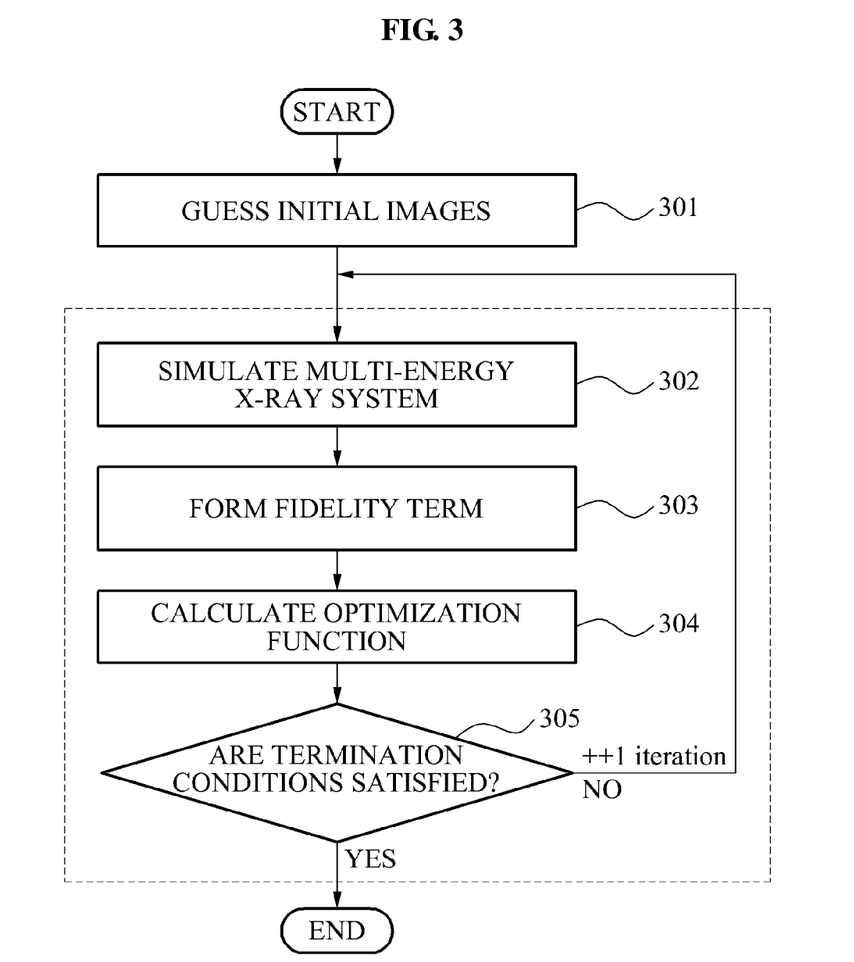
FIG. 3 is a flowchart illustrating an operational method of a material-discriminated image processing unit according to embodiments.

Hereinafter, the operation of the image updating unit 223 according to embodiments will be described in detail with reference to FIG. 3.

In 301, an initial image for each of M materials forming the target 140 is guessed by receiving an input of projection images of each energy band that may be generated when a multi-energy x-ray spectrum of the multi-energy x-ray equipment 110 of FIG. 1 passes through the target 140 consisting of the at least one material.

In 302, a simulation with respect to a multi-energy x-ray system is performed.

As an example, the multi-energy x-ray system according to embodiments may be simulated based on the initial image acquired in 301. The simulated multi-energy x-ray system may be expressed by Equation 1.

$$Y_j(r) = \int_{E_{j1}}^{E_{j2}} I_j(E) \exp(-F_j(x(r), E)) \, dE + n_j(r) \quad \text{[Equation 1]}$$

Y in the left term denotes an image guessed by the multi-energy x-ray system in a $j^{th}$ energy band. I in the right term denotes a function based on an effect of a source that is radiated to a target and an effect of a response of a detector, and may correspond to a known function indicating spectrum information of the multi-energy x-ray system. F denotes a function of x and E based on an effect of a composition ratio of materials consisting of a target in a corresponding energy band. j denotes an index of an energy band. r denotes an N-dimensional location vector, for example, (x, y) in a case of a two-dimensional (2D) image, and (x, y, z) in a case of a three-dimensional (3D) image. E denotes an energy variable.

n denotes a noise term. Since an attenuation characteristic may be changed depending on which material is present at a point r of the target, an internal structure of the target may be displayed in an x-ray image. However, when integration is performed with respect to all energy bands, a difference in an attenuation characteristic between materials may be smoothened and thus, displaying the internal structure of the target may be difficult. Accordingly, in the multi-energy x-ray system according to embodiments expressed by Equation 1, a plurality of x-ray images may be acquired by dividing an integral section from 0 through infinity into N areas.

A value to be found in the multi-energy x-ray system function simulated as expressed by Equation 1 may correspond to x(r). In one aspect, an optimal value of x(r) may be found through a predetermined number of iterations.

After the multi-energy x-ray system is simulated using a function Y(r) in 302, a fidelity term is formed in 303, as one of schemes of finding a value of x(r) included in the corresponding function Y(r). The fidelity term may refer to a term that may express a similarity to a measurement of the multi-energy x-ray system according to embodiments. For ease of description, a Poisson log-likelihood function may be used as the fidelity term in 303. An identity between a Poisson log-likelihood and a Kullback-Leibler divergence, mathematically demonstrated, may be used, and an Iterative Coordinate Descent using Newton-Raphson (ICD/NR) technique of updating an image for each pixel using an NR scheme may be applied.

As an example, when $$F_j(x, E) = \sum_i \mu_i(E_k) L_i$$

in Equation 1, and a vector type is defined as $$\frac{1}{2}(L - \hat{L})^T A(L - \hat{L}) - b^T L,$$

the fidelity term may be expressed by Equation 2.

$$A = \sum_k \left( \mu(E_k) \mu^T(E_K) \left( \sum_j I_j(E_k) \exp\left( -\sum_i \mu_i(E_k) \hat{L}_i \right) \right) \right)$$

$$b = \sum_j (1 - w_j) \cdot \left( \sum_k I_j(E_k) \exp\left( -\sum_i \mu_i(E_k) \hat{L}_i \right) \mu(E_k) \right)$$

[Equation 2]

Here, $$w_j = \frac{Y_j}{\sum_k I_j(E_k) \exp\left( -\sum_i \mu_i(E_k) \hat{L}_i \right)}.$$

In Equation 2, $\mu_i(E_k)$ denotes an attenuation characteristic curve based on energy of an $i^{th}$ material in a $k^{th}$ updating procedure. $L_i$ denotes an amount of the $i^{th}$ material, that is, a length of the $i^{th}$ material. The function F defined in Equation 2 is an example provided for ease of explanation, and may be defined in other schemes depending on configurations.

In 304, an optimization function is calculated using the fidelity term formed in 303. Operation 304 may correspond to an operation of calculating a correction value by which a predetermined cost function using the fidelity term formed in 303 may be minimized, and updating an initial image to a material-discriminated image by applying the correction value to the initial image. As aforementioned, the operation 304 may be performed based on pixels, blocks, or images.

According to other embodiments, the optimization function may be calculated by further incorporating a predetermined regularization term to the fidelity term formed as expressed by Equation 2.

When a quadratic regularization term is used as an example of the predetermined regularization term, a determinant corresponding to (A+R)x=b may need to be solved. When a non-quadratic regularization term is used, the optimization function may be solved using an equation. As an example, when a quadratic regularization term is used, the matrix A of Equation 2 may be replaced with Equation 3.

$$A' = A + \gamma R$$ [Equation 3]

In Equation 3, a measurement of an amount of a material updated with respect to the given $\hat{L}_i$ may be obtained using an inverse matrix calculation.

When the material-discriminated image is generated by updating the initial image in 304, a predetermined number of iterations is performed in 305. Through the iterations, a material-discriminated image having better quality may be acquired.

Referring again to FIG. 2, the image updating unit 223 may update an initial image to a material-discriminated image using the method described with reference to FIG. 3. When the predetermined number of iterations performed in 305 of FIG. 3 is terminated, a material-discriminated image with respect to each of the M materials may be output.

The output material-discriminated image may be input to an image signal processing unit (now shown), and may be converted to an image to be displayed, that is, an image in which material-discriminated images are overlaid. The converted image may be output through the display 130.

<Embodiment 1 Using an Apparatus for Discriminating a Multi-Energy X-Ray Material from an Image>

Figure 4:
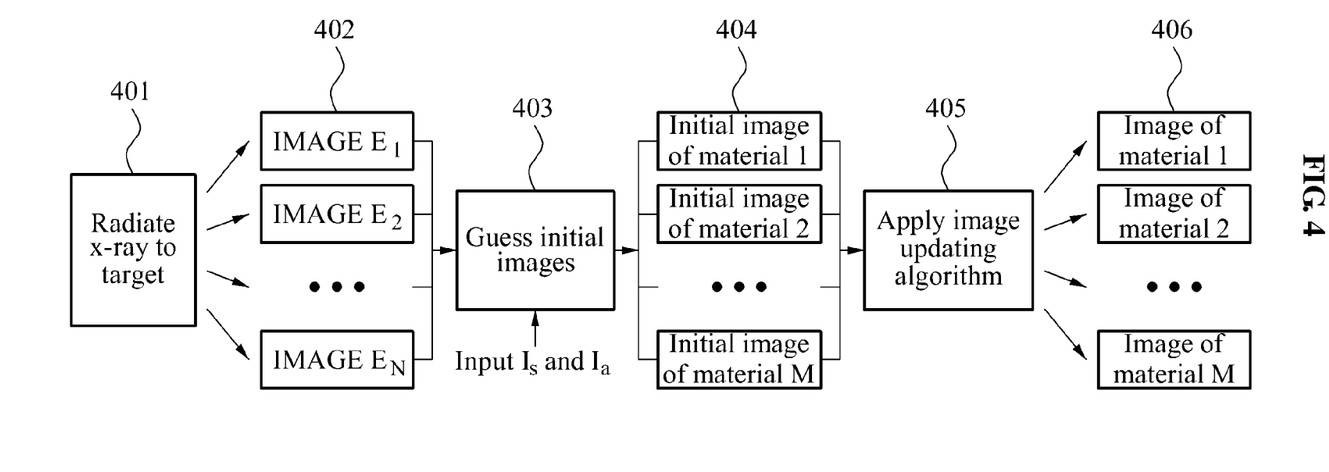
FIG. 4 is a diagram illustrating an operational method of a multi-energy x-ray system according to embodiments.

FIG. 4 illustrates an operational method of a multi-energy x-ray system according to embodiments.

As aforementioned with reference to FIGS. 2 and 3, a multi-energy x-ray system according to embodiments may be operated as described below.

In 401, respective projection images of energy bands that may be generated when a multi-energy x-ray spectrum of a multi-energy x-ray equipment unit passes through a target consisting of at least one material are received. In 402, the received projection images include images $E_1$ through $E_N$ corresponding to N energy bands of the multi-energy x-ray spectrum.

In 403, with respect to the images $E_1$ through $E_N$, initial images are guessed using multi-energy spectrum information $I_s$ and an attenuation characteristic $I_a$ for each material. As a result of guessing the initial images, initial images of materials forming a target, from an initial image of a material 1 to an initial image of a material M, are acquired in 404.

In 405, an image updating algorithm, according to embodiments, is applied to the guessed initial images from the initial image of the material 1 to the initial image of the material M. As a result of applying the image updating algorithm, images of the materials, from an image of the material 1 to an image of the material M are acquired in 406. In 406, a predetermined number of iterations may be performed.

<Embodiment 2 Using an Apparatus for Discriminating a Multi-Energy X-Ray Material from an Image>

Figure 5:
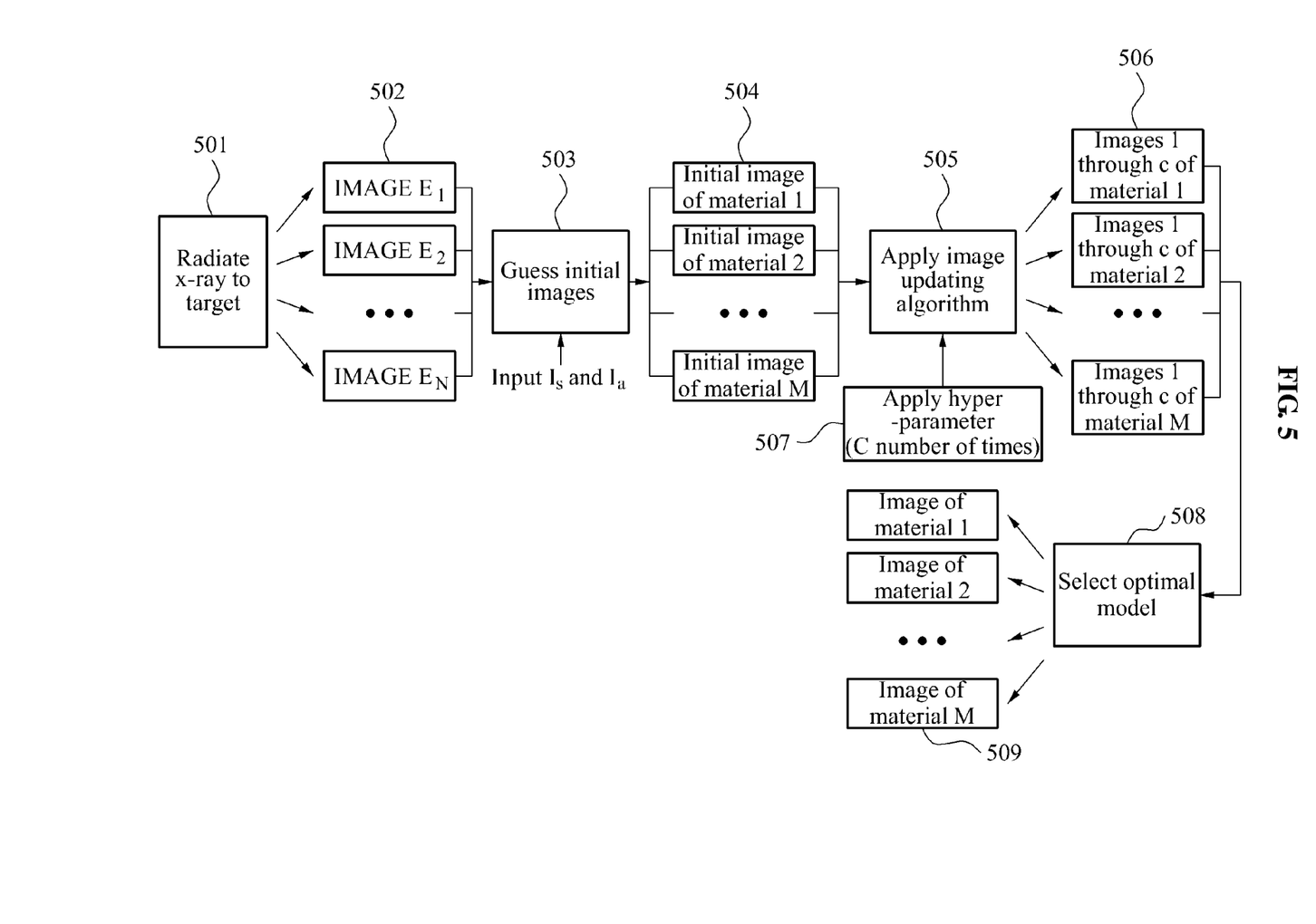
FIG. 5 is a diagram illustrating an operational method of a multi-energy x-ray system according to other embodiments.

FIG. 5 illustrates an operational method of a multi-energy x-ray system according to other embodiments.

In an embodiment illustrated in FIG. 5, a method of selecting an optimal model from material-discriminated images acquired through a C number of attempts using hyper-parameter sets associated with a composition ratio with respect to M materials forming a target may be employed when it is difficult to discriminate the M materials forming the target, directly. As an example, when the target corresponds to a tissue from a human body, and the like, a method of classifying bones, water, and fat forming a human body into a soft tissue corresponding to the water and the fat, and a hard tissue corresponding to the bones, and setting a hyper-parameter to control the bones, the water, and the fat may be used.

In 501, respective projection images of energy bands that may be generated when a multi-energy x-ray spectrum of a multi-energy x-ray equipment unit passes through a target consisting of at least one material are received. In 502, the received projection images include images $E_1$ through $E_N$ corresponding to N energy bands of the multi-energy x-ray spectrum.

In 503, with respect to the images $E_1$ through $E_N$, initial images are guessed using multi-energy spectrum information $I_s$ and an attenuation characteristic $I_a$ for each material. As a result of guessing the initial images, initial images of materials forming a target, from an initial image of a material 1 to an initial image of a material M, are acquired in 504.

In 505, an image updating algorithm, according to embodiments, is applied to the guessed initial images from the initial image of the material 1 to the initial image of the material M. In this instance, a predetermined number of iterations, for example, a C number of iterations, is performed by applying a hyper-parameter, in 507. As a result of applying the image updating algorithm, images from images 1 through C of the material 1 to images 1 through C of the material M are acquired in 506.

In 508, optimal models are selected by applying a predetermined optimal model selecting algorithm, with respect to the images acquired in 506, from the images 1 through C of the material 1 to the images 1 through C of the material. As a result of applying the predetermined optimal model selecting algorithm, images from an image of the material 1 to an image of the material M are acquired in 509.

In 508, a hyper-parameter set showing best results during the C number of iterations may be selected. The hyper-parameter set may be selected based on a residual value, a weighted residual value, a likelihood value, or the like.

In FIG. 5, a routine may be terminated when optimal models are selected by applying a hyper-parameter and images from an image of the material 1 to an image of the material M are acquired. In this instance, the image updating algorithm applied in 506 may be applied once again, depending on configuration. Otherwise, when a result of discriminating materials with respect to a change in hyper-parameter is predictable, the image updating algorithm applied in 506 may be applied again after reducing the unknown quantity M by re-calculating a result of applying the hyper-parameter, and M material-discriminated images may be acquired.

<Embodiment 3 Using an Apparatus for Discriminating a Multi-Energy X-Ray Material from an Image>

Figure 6:
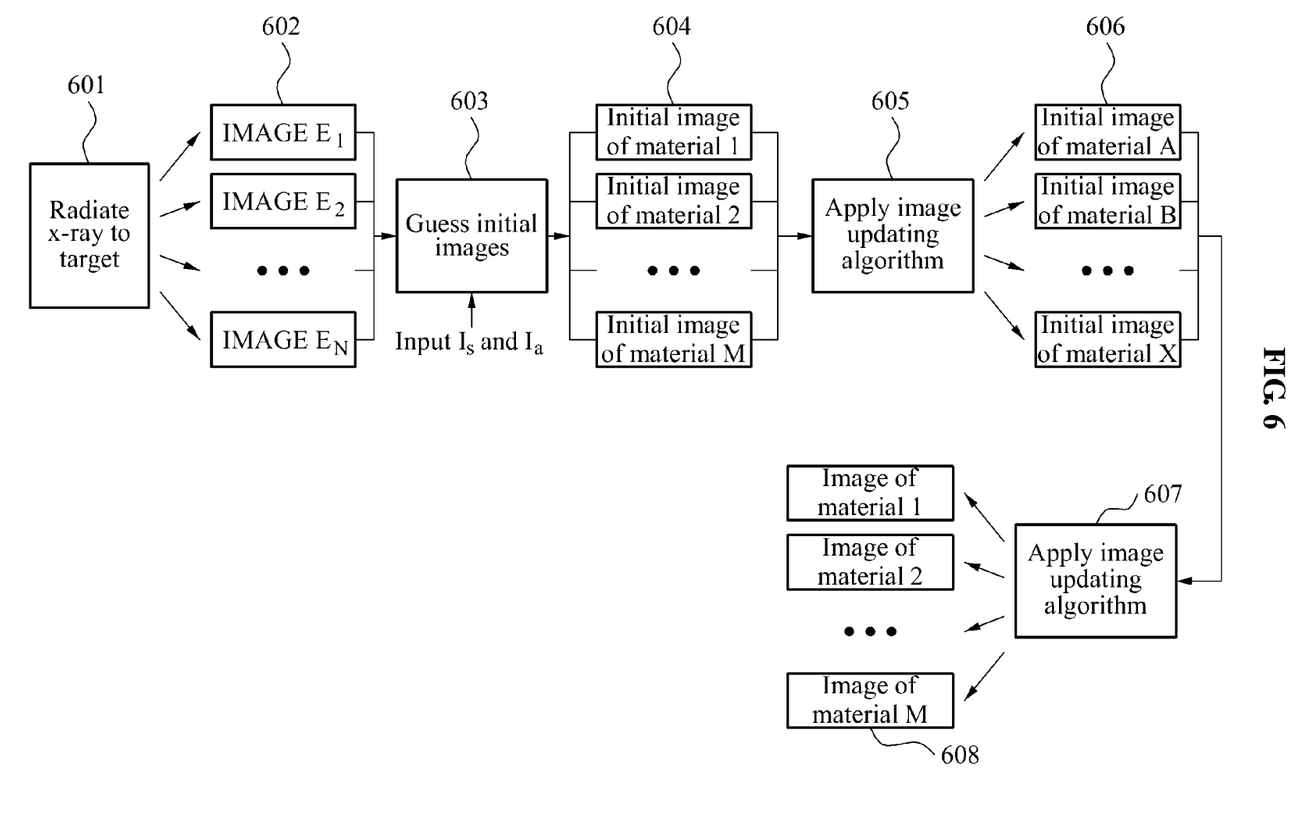
FIG. 6 is a diagram illustrating an operational method of a multi-energy x-ray system according to still other embodiments.

FIG. 6 illustrates an operational method of a multi-energy x-ray system according to still other embodiments.

In an embodiment illustrated in FIG. 6, a method of acquiring composition-discriminated images with respect to essential elements constituting M materials forming a target, for example, carbon C, hydrogen H, oxygen O, nitrogen N, and the like, and then acquiring material-discriminated images by applying an image updating algorithm to the composition-discriminated images may be employed. As an example, when the target corresponds to a tissue from a human body, and the like, elements composing the corresponding tissue are well-known and thus, initial images with respect to the elements may be acquired, and material-discriminated images may be acquired by updating the initial images.

In 601, respective projection images of energy bands that may be generated when a multi-energy x-ray spectrum of a multi-energy x-ray equipment unit passes through a target consisting of at least one material are received. In 602, the received projection images include images $E_1$ through $E_N$ corresponding to N energy bands of the multi-energy x-ray spectrum.

In 603, with respect to the images $E_1$ through $E_N$, initial images are guessed using multi-energy spectrum information $I_s$ and an attenuation characteristic $I_a$ for each material. As a result of guessing the initial images, initial images of materials forming a target, from an initial image of a material 1 to an initial image of a material M, are acquired in 604.

In 605, an image updating algorithm, according to embodiments, is applied to the guessed initial images from the initial image of the material 1 to the initial image of the material M. As a result of applying the image updating algorithm, initial images of materials forming the target, from an initial image of a material A to an initial image of a material X, are acquired in 606.

In 607, the image updating algorithm is applied to the initial images that are acquired in 606, from the initial image of the material A to the initial image of the material X. As a result of applying the image updating algorithm, images from an image of the material 1 to an image of the material X are acquired in 608.

The method according to the above-described embodiments may be recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described embodiments, or vice versa.

Although a few example embodiments have been shown and described, the present disclosure is not limited to the described example embodiments. Instead, it would be appreciated by those skilled in the art that changes may be made to these example embodiments without departing from the principles and spirit of the disclosure, the scope of which is defined by the claims and their equivalents.

The invention claimed is:

1. An apparatus for discriminating a multi-energy x-ray material from an image, the apparatus comprising:
   a table configured to record attenuation information and multi-energy x-ray spectrum information corresponding to at least one material;
   an initial image guessing unit configured to guess an initial image of each of the at least one material with respect to a projection image of each energy band that is generated when a multi-energy x-ray spectrum passes through a target consisting of the at least one material; and
   an image updating unit configured to perform an update of the initial image to a material-discriminated image, based on the guessed initial image, the spectrum information recorded in the table, and the attenuation information recorded in the table.

2. The apparatus of claim 1, wherein the initial image guessing unit is configured to guess the initial image based on energy distribution information for each of the at least one material.

3. The apparatus of claim 1, wherein the image updating unit is configured to perform the update based on pixels constituting the initial image.

4. The apparatus of claim 1, wherein the image updating unit is configured to calculate a correction value by which a predetermined cost function is minimized, and update the initial image to the material-discriminated image by applying the calculated correction value to the initial image.

5. The apparatus of claim 4, wherein the image updating unit is configured to iterate the update, a predetermined number of times, by feeding back the initial image to which the calculated correction value is applied as an input of the image updating unit.

6. The apparatus of claim 1, wherein the image updating unit is configured to update the initial image as the material-discriminated image, further based on a hyper-parameter associated with the at least one material.

7. The apparatus of claim 6, wherein the hyper-parameter corresponds to a composition ratio of the at least one material.

8. A method of acquiring a multi-energy x-ray image, the method comprising:
   receiving a projection image of each energy band that is generated when a multi-energy x-ray spectrum passes through a target consisting of at least one material;
   guessing an initial image for each of the at least one material based on the projection image; and
   acquiring a material-discriminated image with respect to each of the at least one material, by applying an image updating algorithm to the initial image.

9. The method of claim 8, wherein the guessing comprises guessing the initial image based on energy distribution information for each of the at least one material.

10. The method of claim 8, wherein the image updating algorithm is applied based on pixels constituting the initial image.

11. The method of claim 8, wherein the acquiring comprises calculating a correction value by which a predetermined cost function is minimized, and updating the initial image to the material-discriminated image by applying the calculated correction value to the initial image.

12. The method of claim 11, wherein the acquiring further comprises re-calculating the correction value, a predetermined number of times, with respect to the initial image to which the calculated correction value is applied, and performing feedback for applying the re-calculated correction value to the initial image.

13. The method of claim 8, wherein the acquiring comprises updating the initial image to the material-discriminated image, further based on a hyper-parameter associated with the at least one material.

14. The method of claim 13, wherein the hyper-parameter corresponds to a composition ratio of the at least one material.

15. A non-transitory computer-readable medium comprising a program for instructing a computer to perform the method of one of claims 8 to 14.

16. A multi-energy x-ray system, comprising:
   a multi-energy x-ray equipment unit configured to radiate a multi-energy x-ray spectrum; and
   a material-discriminated image processing unit configured to acquire a material-discriminated image with respect to each of at least one material, by receiving a projection image of each energy band that is generated when the multi-energy x-ray spectrum passes through a target consisting of the at least one material,
   wherein the material-discriminated image processing unit comprises:
   a table configured to record attenuation information and multi-energy x-ray spectrum information corresponding to the at least one material;
   an initial image guessing unit configured to guess an initial image of each of the at least one material with respect to the projection image of each energy band that is generated when the multi-energy x-ray spectrum passes through the target consisting of the at least one material; and
   an image updating unit configured to perform an update of the initial image to the material-discriminated image, based on the guessed initial image, the spectrum information recorded in the table, and the attenuation information recorded in the table.

* * * * *